(12) United States Patent
Wani et al.

(10) Patent No.: US 6,905,710 B2
(45) Date of Patent: Jun. 14, 2005

(54) PHARMACEUTICAL COMPOSITION USEFUL FOR INHIBITION OF OSTEOCLAST FORMATION AND A PROCESS FOR THE EXTRACTION OF MUSSEL HUDROLYSATE FROM INDIAN GREEN MUSSEL

(75) Inventors: Mohan Ramachandra Wani, Pune (IN); Pradeep Bhaskar Parab, Pune (IN); Anil Chatterji, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 331 days.

(21) Appl. No.: 09/944,497

(22) Filed: Aug. 31, 2001

(65) Prior Publication Data

US 2003/0044470 A1 Mar. 6, 2003

(51) Int. Cl.⁷ .......................... A61K 35/56; C12P 21/06
(52) U.S. Cl. ..................................... 424/547; 435/68.1
(58) Field of Search .......................... 424/547; 435/68.1

*Primary Examiner*—Christopher R. Tate
*Assistant Examiner*—Randall Winston
(74) *Attorney, Agent, or Firm*—Baker Botts, L.L.P.

(57) ABSTRACT

The invention provides a compositions comprising mussel hydrolysate from Indian green mussel, e.g., *Perna viridis*. The invention further provides methods of inhibiting or preventing osteoclast formation and/or bone resorption comprising administration of mussel hydrolysate from Indian Green to an animal or human. The compositions of the invention are non-toxic to other cells. Additionally, the invention provides processes for extracting mussel hydrolysate from Indian green mussel, e.g., *Perna viridis*.

24 Claims, 5 Drawing Sheets

PHARMACEUTICAL COMPOSITION USEFUL FOR INHIBITION OF OSTEOCLAST FORMATION AND A PROCESS FOR THE EXTRACTION OF MUSSEL HUDROLYSATE FROM INDIAN GREEN MUSSEL

FIELD OF THE INVENTION

The present invention relates to an extract from the Indian green mussel (*Perna viridis*) that inhibits osteoclast formation and bone resorption. The present invention further relates to a pharmaceutical composition comprising an extract of Indian green mussel. Further, the present invention relates to a process of extraction of mussel hydrolysate from Indian green mussel.

BACKGROUND OF INVENTION

Bone is a metabolically active and highly organized tissue. Bone contains two distinct cell types, the osteoblasts or bone forming cells and the osteoclasts, or bone resorbing cells. Bone remodeling is a normal process that involves the resorption of bone by osteoclasts and the synthesis of bone matrix by osteoblasts. These two processes are normally integrated to maintain both the structural integrity of the skeletal system and homeostasis of bone. Both these processes are influenced by a wide variety of systemic and local factors. An imbalance of osteoblast and osteoclast functions can arise from variety of hormonal changes or perturbations of inflammatory and growth factors resulting in skeletal abnormalities characterized by increased or decreased bone mass. This may lead to excessive bone loss and eventually fracture.

Osteoclasts are specialized monocyte/macrophage family members that differentiate from hemopoietic precursors. Increased osteoclast activity is seen in osteoporosis (Gross et al., 1996), rheumatoid arthritis (Seitz and Hunstein, 1985), Paget's disease (Siris, 1999), and many other diseases of clinical importance. In these disorders bone resorption exceeds bone formation, resulting in decreased skeletal mass. This causes bones to become thin, fragile and susceptible to fracture. The consequences of osteoporotic bone fractures include chronic pain in bone, body deformity including height loss and muscle weakness.

Osteoporosis is now a serious problem that imposes substantial limitations on the affected individuals. In humans, 1 in 3 women and 1 in 12 men over 45 years are at risk of suffering painful and deforming fractures as a result of osteoporosis. More women die after hip fractures than from cancers of ovaries, cervix and uterus. Osteoporosis occurs at an earlier age in Indian males and females compared to western countries (Gupta, 1996).

Most bone diseases occur due to increased osteoclast activity and increased bone resorption. Bone resorption and loss of calcium from bone are complications associated with arthritis, many cancers and with bone metastases of breast and prostate tumors. Current treatment for these diseases primarily targets osteoclasts.

Drugs that inhibit the formation or activity of osteoclasts are valuable for treating these diseases. However, a variety of disadvantages are associated with current therapeutic agents (such as estrogen and selective estrogen receptor modulators, bisphosphonates and calcitonin) used in osteoporosis and other metabolic bone disorders (Rodan and Martin, 2000). Drugs developed for treating osteoporosis and related disorders showed adverse events and contraindications (Watts, 1999). The side effects of current therapies include increase in the risk of breast and uterine cancers, upper gastrointestinal distress and induction of immune responses.

Drugs that inhibit the formation or activity of osteoclasts and with no toxicity and harmful side effects will be valuable for treating osteoporosis, Paget's disease, and inflammation of bone associated with rheumatoid arthritis or periodontal disease.

Natural products from plants and organisms have frequently been used as a source for development of effective drugs. There is an increased interest in analysis of natural products from marine organisms. Sea animals contain metabolites which can be used for treatment of many diseases.

An extract from mussels was first shown to have the anti-inflammatory activity in rats (Miller and Ormrod, 1980). In these studies, a preparation from New Zealand green mussel (*Perna canaliculus*) effectively reduced the rat paw edema but only if injected into the peritoneal cavity. Freeze-dried extract preparations from mussels have been used as anti-inflammatory treatments (Caughey et al., 1983). A preliminary report on the use of mussel hydrolysate obtained from mussel meat by acid hydrolysis indicated that the hydrolysate had virus-inhibiting activity against influenza viruses (Bichurina et al., 1994).

The extract prepared from the Indian green mussel (*Perna viridis*) has previously been found to be active against all influenza, herpes and hepatitis viral strains. The extract is also found to possess not only prophylactic efficacy for protection from several viral diseases but it also shows a high therapeutic property against these diseases.

A process for extracting mussel hydrolysate is disclosed in an unpublished, pending, process patent application filed by the National Institute of Oceanography, Goa, India (Patent No. 493/DEL/99) on Mar. 31, 1999.

In the present invention, an attempt has been made to study the effect of extract prepared from the Indian green mussel on osteoclast differentiation and bone resorption in vitro.

SUMMARY OF THE INVENTION

The present invention relates to compositions comprising an extract from Indian green mussel. The invention further relates to a compositions that inhibits osteoclast formation and/or bone resorption. The compositions are non-toxic to other cells and may be administered orally or parenterally to animals and humans. This composition may be useful for treatment of bone loss due to osteoporosis, rheumatoid arthritis, Paget's disease of bone, and other metabolic bone disorders. Further, the invention provides a process of extraction of mussel hydrolysate from Indian green mussel (*Perna viridis*). The invention further relates to methods of inhibiting osteoclast formation and/or bone resorption.

DETAILED DESCRIPTION OF THE INVENTION

Figure 1:
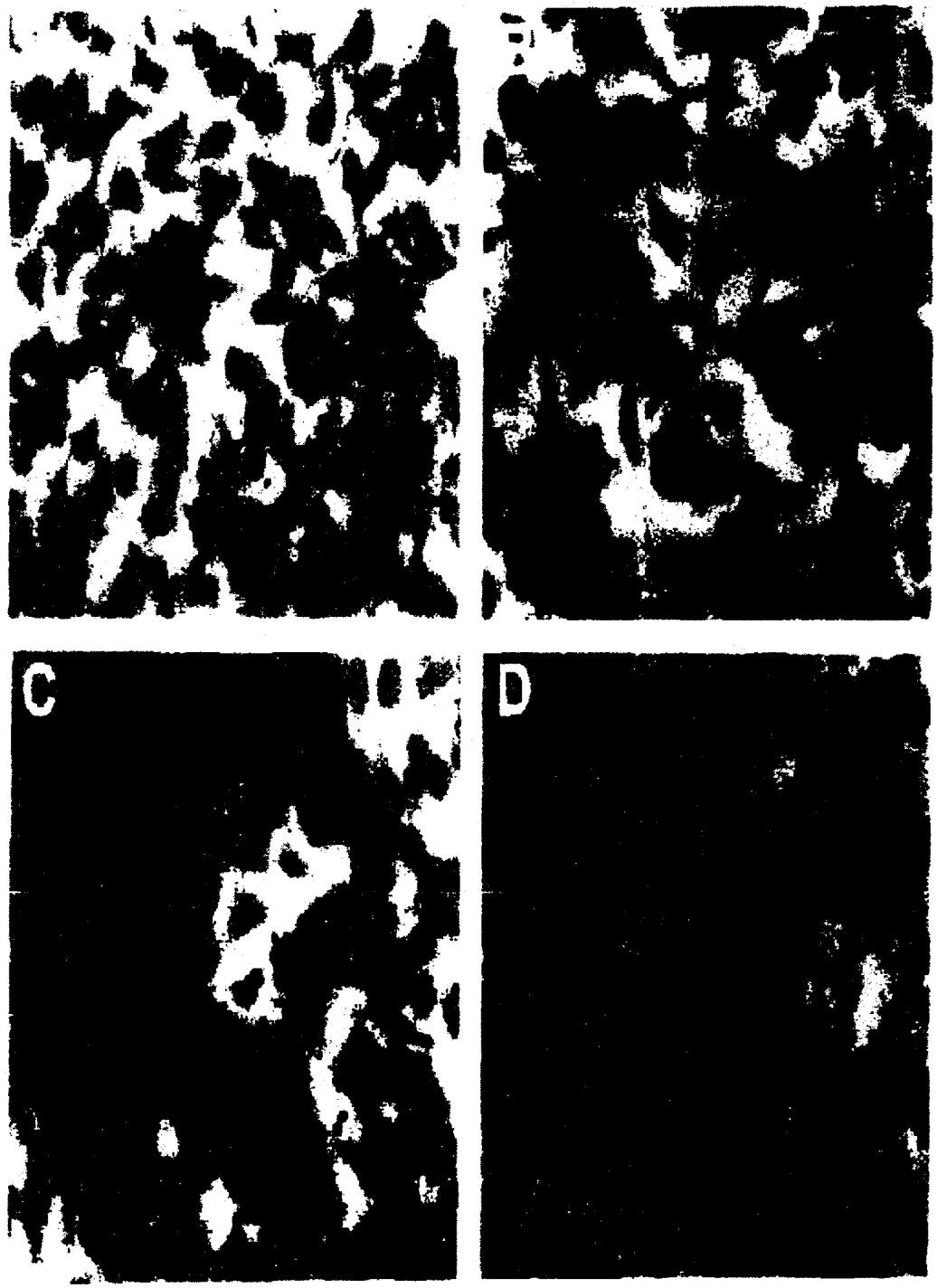
FIG. 1: Mussel hydrolysate inhibits formation of TRAP-positive red osteoclasts. Tartrate-resistant acid phosphatase (TRAP) staining of M-CSF-dependent non-adherent bone marrow cells incubated for 7 days on coverslips in a 96-well plate with (A) 30 ng/mL M-CSF; (B) M-CSF and 30 ng/mL RANKL; (C) M-CSF and 30 ng/mL RANKL and 100 µg/mL mussel hydrolyaste. Cells expressing TRAP are stained red. Magnification 360×

The present invention provides methods and compositions for inhibiting osteoclast formation and/or bone resorption. Compositions of the invention comprise an extract of Indian green mussel. In preferred embodiments of the invention, the extract is mussel hydrolysate from *Perna viridis*. In some nonlimiting embodiments, the invention provides pharmaceutical compositions, comprising an extract of Indian green mussel, useful for the inhibition of the osteoclast formation in animals and humans. In some non-limiting embodiments of the invention, the pharmaceutically acceptable composition comprises mussel hydrolysate from an Indian green mussel. The invention further contemplates the use of pharmaceutically acceptable additives such as carbohydrates, sugar, proteins, fats, excipients and diluents in compositions of the invention. Compositions of the invention may be administered to animals or humans orally or parenterally.

According to the present invention the term "osteoclast formation" means differentiation of an osteoclast precursor cells cell or its progeny into a cell that is identifiable as an osteoclast based on the presence of one or more molecular markers and/or cytological traits.

According to the present invention the term "osteoclast activity" refers to one or more cellular processes that cause or contribute to bone resorption in vitro or in vivo.

Compositions of the invention may be used to inhibit formation of mononuclear and/or multinuclear tartrate-resistant acid phosphatase (TRAP)-positive osteoclasts in vitro or in vivo. Compositions of the invention may be used to inhibit osteoclastogenesis in murine hemopoietic stem cells in vitro or in vivo. Compositions of the invention may have few or no toxic effects on other cell types in vitro or in vivo. Compositions of the invention may be used to inhibit bone resorption in vitro or in vivo.

The invention also provides methods of inhibiting osteoclast formation and/or bone resorption. In some non-limiting embodiments, the methods of inhibiting osteoclast formation and/or bone resorption comprise contacting bone marrow cells with a composition comprising mussel hydrolysate. The concentration of mussel hydrolysate in a composition having a liquid form is preferably greater than about 10 µg/mL and more preferably greater than 30 µg/mL. The concentration of mussel hydrolysate in liquid compositions of the invention may exceed about 100 µg/mL. In some non-limiting embodiments of the invention, methods of inhibiting osteoclast formation and/or bone resorption comprise administration of a pharmaceutical composition comprising mussel hydrolysate and at least one additive to a human or animal.

In preferred embodiments of the invention, formation of multinuclear and/or mononuclear TRAP-positive osteoclasts is inhibited by at least about 20% and more preferably by at least about 50%. In preferred embodiments of the invention, receptor activator of NF-κB ligand (RANKL)-induced bone resorption is inhibited by at least about 40% and more preferably at least about 70%.

The invention further provides a process for the extraction of mussel hydrolysate from the Indian green mussel. In some non-limiting embodiments of the invention, the mussel hydrolysate is obtained by the following process:

meat and mantle fluid of Indian green mussel is obtained;

meat and mantle fluid are fermented with protosubtiline (6% of the weight of meat) and 6% distilled water at a constant temperature of 40° C. for two hours thereby forming a thick paste;

the thick paste (12% of the total meat weight) is digested with concentrated hydrochloric acid for 15 hours at 100° C.±2° C.;

the resulting solution is cooled to room temperature and pH is maintained by adding sodium hydroxide;

the resulting solution is incubated in a separating flask for a few days the active extract is obtained by removing the middle part of the solution.

In some non-limiting embodiments of the invention, the mussel hydrolysate is obtained by the following process:

meat and mantle fluid of Indian green mussel is obtained;

meat and mantle fluid are fermented with a proteolytic enzyme at a constant temperature thereby forming a thick paste;

the thick paste is digested with an acid, the resulting solution is adjusted to room temperature and pH is maintained by adding a base;

the resulting solution is incubated in a separating flask;

the active extract is obtained by removing the middle part of the solution.

The process may further comprise combining meat and mantle fluid with an amount of distilled water that is equal to 6% of the mass of meat or the total mass of meat prior to or during the fermentation step.

In some non-limiting embodiments of the invention, the mussel hydrolysate is obtained by the following process:
- obtaining meat along with the mantle fluid of Indian green mussel;
- fermenting meat with mantle fluid with enzyme protosubtiline;
- fermenting 6% of the weight of meat with 6% distilled water at a constant temperature;
- digesting the thick paste with concentrated hydrochloric acid;
- digesting 12% of the total meat weight for 15 hours at 100° C.±2° C.;
- cooling the resulting solution at room temperature and maintaining the maintaining the pH of the solution by adding sodium hydroxide; and
- isolating the active extract by keeping the resulting solution in a separating flask for a few days and removing the middle part of the solution.

In some non-limiting embodiments of the invention, meat with mantle fluid is fermented with enzyme protosubtiline (6% of the weight of meat) and 6% distilled water at a constant temperature of 40° C. for two hours to obtain a thick paste. In some non-limiting embodiments of the invention, the thick paste is digested with concentrated hydrochloric acid (12% of the total meat weight) for 15 hours at 100° C.±2° C. to produce a solution. In some non-limiting embodiments of the invention, the resulting solution is cooled to room temperature and the pH of the solution is maintained by adding sodium hydroxide. In some non-limiting embodiments of the invention, the active extract is isolated by keeping the resulting solution in a separating flask for 10 days and carefully removing the middle part of the solution.

Advantages of the present invention include:
1) Mussel hydrolysate obtained from the Indian green mussel (*Perna viridis*) inhibits osteoclast formation from hemopoietic osteoclast precursors in mice.
2) Mussel hydrolysate obtained from the Indian green mussel (*Perna viridis*) inhibits bone resorption in mice.
3) Mussel hydrolysate is non-toxic to other cells and will be useful to prepare a drug that may be administered orally rather than parenterally.
4) Mussel hydrolysate may be useful for the treatment of bone loss in osteoporosis, rheumatoid arthritis, Paget's disease of bone and other metabolic diseases of clinical importance.

EXAMPLES

The following non-limiting examples are provided to illustrate the present invention. Other embodiments of the invention exist as will be appreciated by persons of ordinary skill in the art. The following experiments were conducted several times with reproducible results.

Example 1
In vitro Method for Inhibition of Osteoclast Formation and Bone Resorption Using Mussel Hydrolysate Comprising
(i) Effect of Mussel Hydrolysate on in vitro Osteoclastogenesis Balb/c mice were sacrificed by cervical dislocation and bone marrow cells were obtained from long bones by a conventional process (Wani et al., 1999). Osteoclasts were generated from a stroma free population of non-adherent, macrophage-colony stimulating factor (M-CSF)-dependent osteoclast precursors from mouse bone marrow cells. These precursors were stimulated with M-CSF and receptor activator of NF-κB ligand (RANKL) to form osteoclasts. Mussel hydrolysate was tested for its effect in these stroma free systems for its ability to modulate differentiation of osteoclast progenitors of the monocyte/macrophage lineage into osteoclasts.

M-CSF-dependent, non-adherent bone marrow cells were harvested, washed twice and resuspended in αxMEM containing 10% foetal bovine serum (FBS). This suspension was added to the wells of a 96-well plate containing coverslips. Cells were incubated in the presence or absence of M-CSF, RANKL and/or mussel hydrolysate, at 37° C. in a humidified atmosphere of 5% $CO_2$ in air. Cultures were fed twice a week by replacing half medium with an equal quantity of fresh medium containing reagents. At varying time intervals, depending upon experimental design, cells on coverslips were prepared for tartrate-resistant acid phosphatase (TRAP) staining.

(ii) Tartrate-Resistant Acid Phosphatase (TRAP) Staining

Osteoclasts express tartrate-resistant acid phosphatase (TRAP) activity. This activity forms the basis of a widely used cytochemical staining assay for identifying osteoclasts in vivo and in vitro. It is claimed that the assay is specific for osteoclasts in bone. In this Example, staining for TRAP was carried out using naphthol AS-BI phosphate as a substrate and pararosaniline chloride as a stain for the reaction product in the presence of sodium tartrate (Fuller et al., 2000). TRAP positive cells (osteoclasts) appear as red cells in FIG. 1.

(ii) Bone Resorption Assay

Osteoclasts have the ability to excavate authentic resorption lacunae in vivo and in vitro. Bone resorption is a unique function of the osteoclast and is therefore the most useful means of distinguishing it from other cell types. M-CSF-dependent, non-adherent bone marrow cells were incubated for 10 days on bovine cortical bone slices in the presence of M-CSF, RANKL with or without mussel hydrolysate. Bone slices were examined for resorption pits by reflected light microscopy as previously described (Wani et al. 1999).

Example 2
Assessment of Inhibition of Osteoclast Formation and Bone Resorption in vitro Using Mussel Hydrolysate In the present study, the effect of mussel hydrolysate was examined first on osteoclast differentiation from mouse bone marrow cells. Stromal cell-free M-CSF-dependent osteoclast precursors were isolated from bone marrow cells and incubated for 7 days. Absence of contaminating stromal cells was confirmed in cultures in which M-CSF was omitted. Osteoclasts induced by RANKL were characterized for the presence of tartrate-resistant acid phosphatase (TRAP) activity, according to the method of Example 1.

Figure 2:
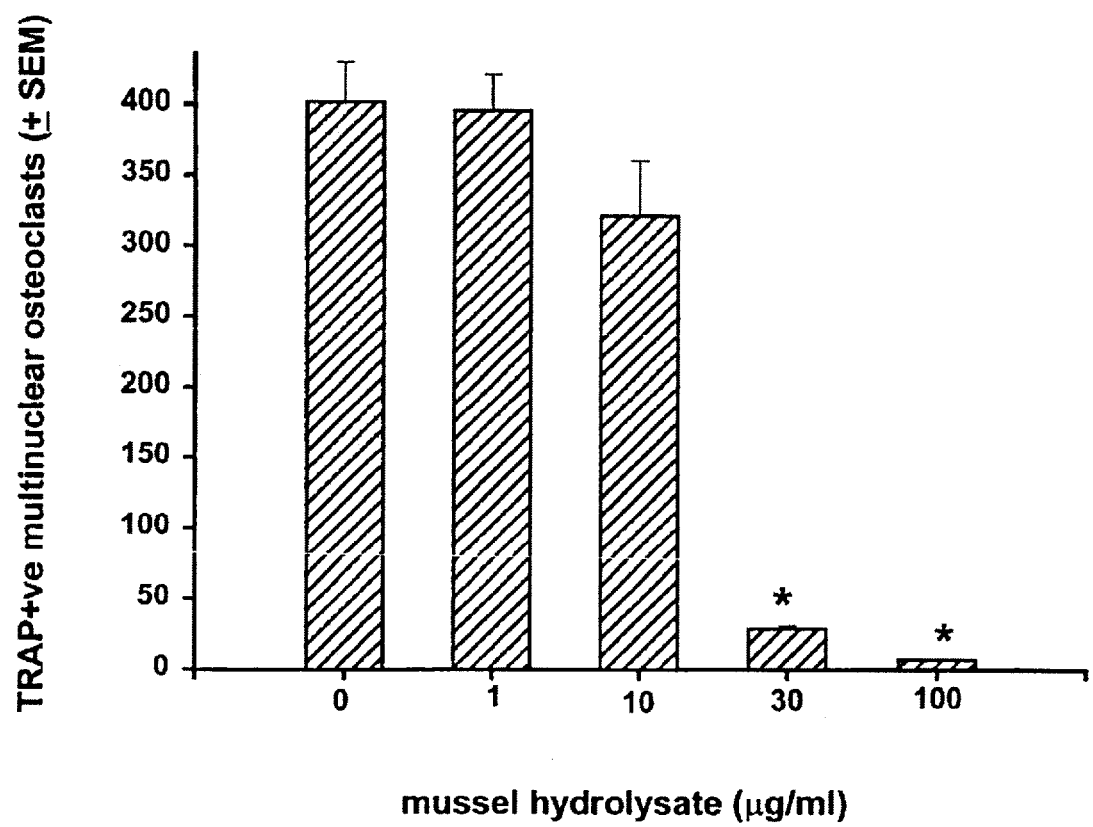
FIG. 2: Mussel hydrolysate dose-dependently inhibits multinuclear TRAP-positive osteoclasts. M-CSF-dependent non-adherent bone marrow cells were incubated for 7 days in a 96-well plate containing coverslips in the presence of 30 ng/mL M-CSF±30 ng/mL RANKL and increasing concentrations of mussel hydrolysate. Cells on coverslips were stained for TRAP activity and TRAP-positive multinuclear cells with at least three nuclei were counted. n=12 cultures per variable. Similar results were obtained in several repeat experiments. *p<0.05 vs. cultures with no added mussel hydrolysate.
Figure 3:
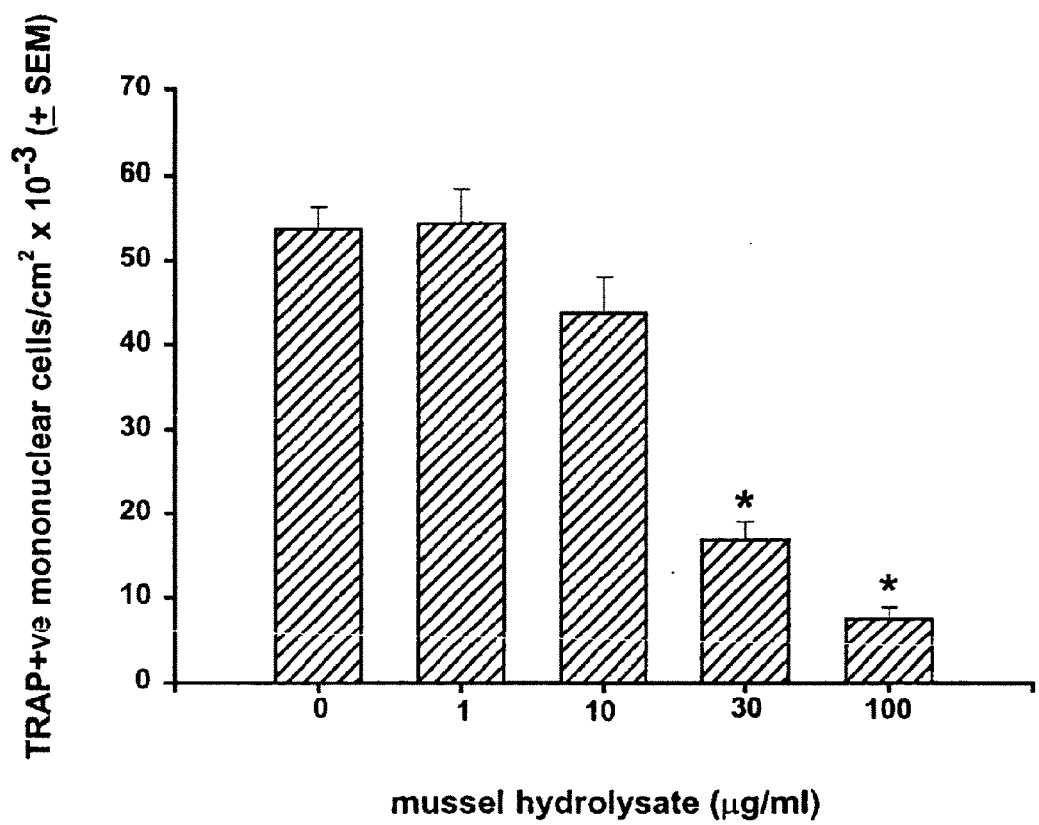
FIG. 3: Mussel hydrolysate dose-dependently inhibits mononuclear TRAP-positive osteoclasts. M-CSF-dependent non-adherent bone marrow cells were incubated for 7 days in a 96-well plate containing coverslips in the presence of 30 ng/mL M-CSF±30 ng/mL RANKL and increasing concentrations of mussel hydrolysate. Cells were stained for TRAP activity and TRAP-positive mononuclear cells with at least three nuclei were counted. n=12 cultures per variable. Similar results were obtained in several repeat experiments. *p<0.05 vs. cultures with no added mussel hydrolysate.

In the presence of M-CSF (30 µg/mL) alone, only macrophages are formed (FIG. 1-A). Large number of TRAP-positive osteoclasts, both mononuclear and multinuclear were formed in these cultures when both M-CSF and RANKL (30 µg/mL) were added (FIG. 1-B). Addition of the mussel hydrolysate dose-dependently inhibited osteoclast formation induced by RANKL (FIGS. 1-C & D). Mussel hydrolysate (30 and 100 µg/mL) significantly inhibited formation of both multinuclear (with 3 or more nuclei)(FIG. 2) and mononuclear (FIG. 3) TRAP-positive osteoclasts. The reduction in the number of osteoclasts formed may be expressed as a percentage of the number of osteoclasts formed in the absence of mussel hydrolysate relative to the number of osteoclasts formed in the presence of mussel hydrolysate. For example, a reduction in mononuclear TRAP-positive osteoclast formation of about 79.5% was observed at a concentration of 10 µg/mL mussel hydrolysate (FIG. 2). Alternatively, inhibition of osteoclast formation may be expressed as the difference between the number of osteoclasts formed in the presence and absence of mussel hydrolysate divided by the number of osteoclasts formed in the absence of mussel hydrolysate. For example, about a 20.5% inhibition of mononuclear TRAP-positive osteoclast formation was observed at a concentration of 10 µg/mL mussel hydrolysate (FIG. 2)

Example 3
Study of Mussel Hydrolysate for Toxicity to Other Cell Types

Figure 4:
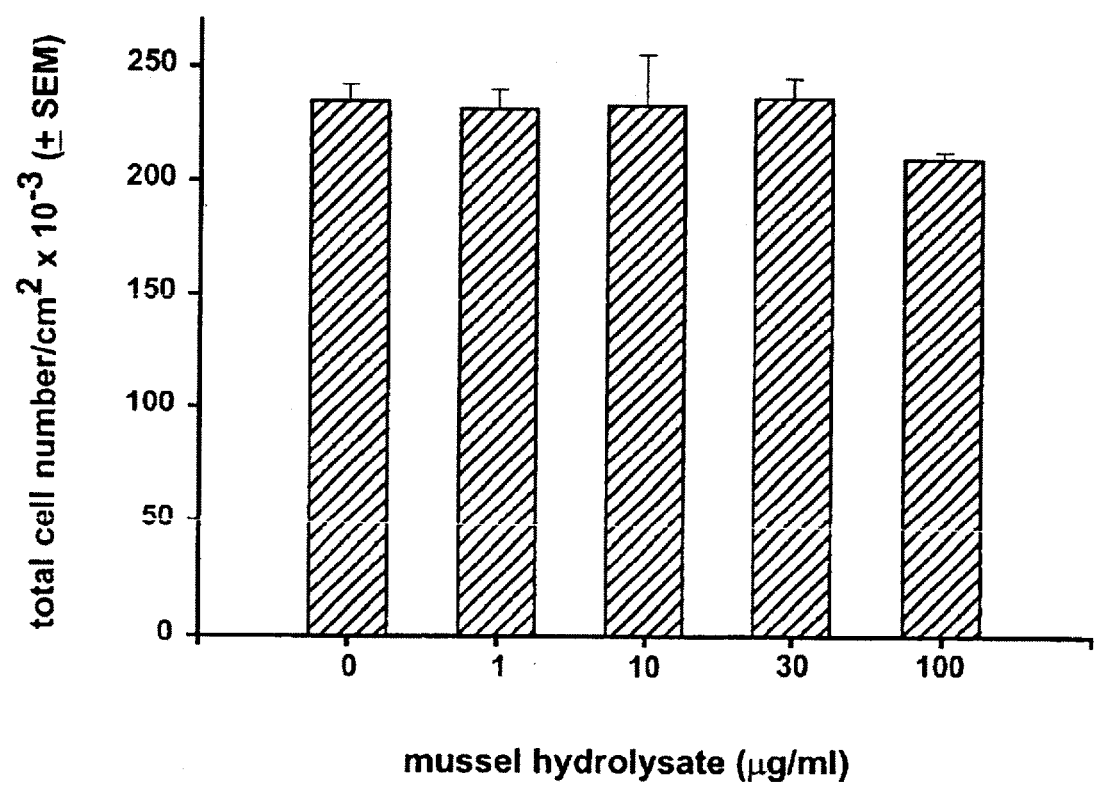
FIG. 4: Mussel hydrolysate is non-toxic to other cell types. M-CSF-dependent non-adherent bone marrow cells were incubated for 7 days in a 96-well plate containing coverslips in the presence of 30 ng/mL M-CSF±30 ng/mL RANKL and increasing concentrations of mussel hydrolysate. The total number of cells (TRAP-positive and TRAP-negative cells) on each coverslip were counted. n=12 cultures per variable. Similar results were obtained in several repeat experiments.

Effect of mussel hydrolysate was also tested for toxicity to other cell types. M-CSF dependent bone marrow cells were incubated in a 96-well plates on cover slips for 7 days in the presence M-CSF (30 µg/mL) and +RANKL (30 µg/mL) and increasing concentration of mussel hydrolysate. The total number of TRAP positive and TRAP-negative cells was counted. The presence of mussel hydrolysate up to 30 µg/mL had no significant effect on the total cell number (FIG. 4). This indicates that mussel hydrolysate is non-toxic to other cell types present in the culture and inhibits only osteoclasts.

Example 4
Mussel Hydrolysate Inhibits Bone Resorption

Figure 5:
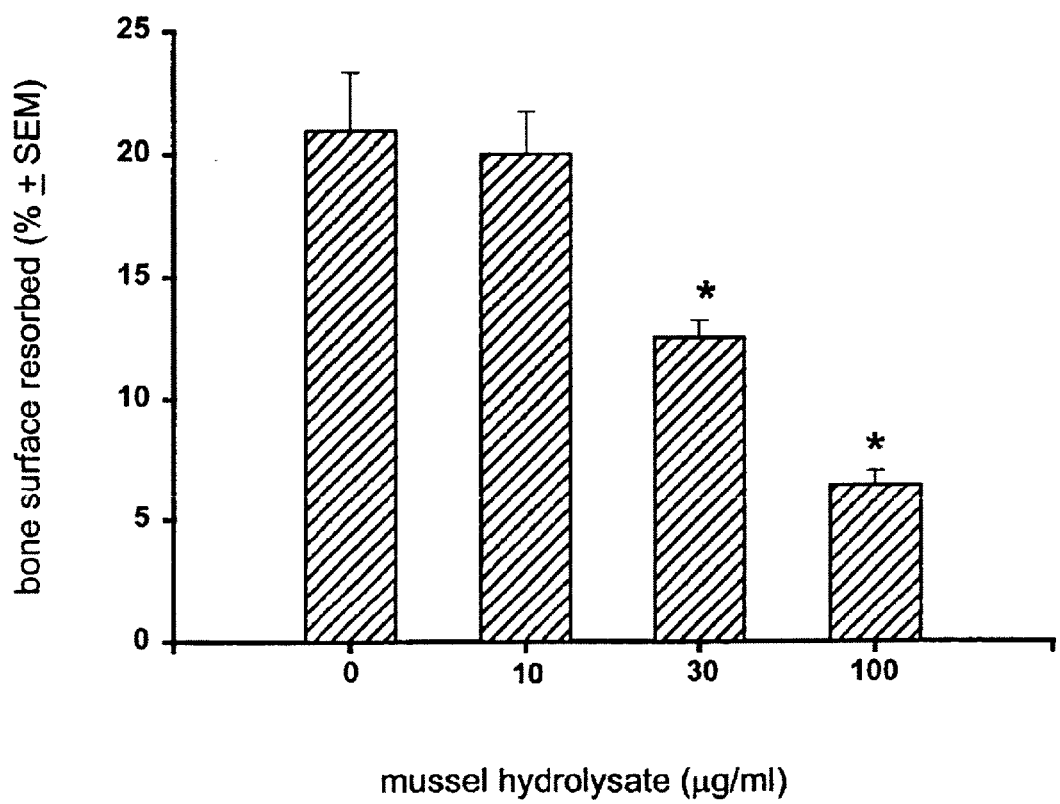
FIG. 5: Mussel hydrolysate dose-dependently inhibits bone resorption. M-CSF-dependent non-adherent bone marrow cells were incubated for 7 days in a 96-well plate containing coverslips in the presence of 30 ng/mL M-CSF±30 ng/mL RANKL and increasing concentrations of mussel hydrolysate. The surface of each bone slice was examined for evidence of bone resorption. Results are expressed from 8 cultures of 2 independent experiments. *p<0.05 vs. cultures with no added mussel hydrolysate.

M-CSF-dependent osteoclast precursors were also incubated for 7 days in 96-well plates containing bovine cortical bone slices in the presence of M-CSF (30 µg/mL) and ±RANKL (30 µg/mL) and various concentrations of mussel hydrolysate. The surface of each bone was examined for evidence of bone resorption. The results are expressed from 8 cultures of 2 independent experiments. Bone resorption was induced by RANKL. It was observed that mussel hydrolysate dose-dependently inhibited bone resorption (FIG. 5).

Example 5
Process for Extracting Mussel Hydrolysate

Mussel hydrolysate may be extracted from Indian green mussel (*Perna viridis*) as follows:
- obtaining meat and mantle fluid of Indian green mussel;
- fermenting meat and mantle fluid with protosubtiline (6% of the weight of meat) and 6% distilled water at a constant temperature of 40° C. for two hours thereby forming a thick paste;
- digesting the thick paste (12% of the total meat weight) with concentrated hydrochloric acid for 15 hours at 100° C.±2° C.;
- cooling the resulting solution at room temperature and maintaining the maintaining pH of the solution by adding sodium hydroxide;
- isolating the active extract by keeping the resulting solution in a separating flask for 10 days and removing the middle part of the solution.

REFERENCES

The references cited throughout this application and listed below are incorporated herein in their entirety by reference.

Bichurina M. A. Nikitina L. E. Sovetova M. G. Rekhina N. 1. Besedina T. V. Boikov I. A & Noskov F. S (1994). The virus-inhibiting activity of a preparation obtained from a mussel hydrolysate. Vopr V/rso/3, 134–136.

Caughey D. E. Grigor R. R. Caughey E. B. Young P Gow P. J & Stewart A. W (1983). *Perna canaliculus* in the treatment of rheumatoid arthritis. *Eur J Rheumatol Inflamm* 6, 197–200.

Fuller K. Lean J. M. Wani M. R & Chambers T. J (2000): A role for TGF in osteoclast differentiation and activation. *J Cell Sci* 113, 2445–2453

Gross C. Eccleshall T. R & Feldman D (1996). Vitamin D receptor gene alleles and osteoporosis. In *Principles of Bone Biology vol.* pp. 917–934. Ed J. P Bilezikian. L. G Raisz. & G. A Rodan. San Diego: Academic Press.

Gupta A (1996). Osteoporosis in India-The nutritional hypothesis. *Natl Med J India* 9, 268–274.

Miller T. E & Ormrod D (1980). The anti-inflammatory activity of *Perna canaliculus* (NZ green mussel). *NZ Med J* 92, 187–193.

Rodan G. A & Martin T. J (2000). Therapeutic approaches to bone diseases. Science 289, 1508–1514.

Seitz M. & Hunstein W (1985). Enhanced prostanoid release from monocytes of patients with rheumatoid arthritis and active systemic lupus erythematosus. *Ann Rheum Dis* 44, 438–445.

Siris E. S (1999). Paget's disease of bone. In *Primer on the Metabolic Bone Diseases and Disorders of Mineral Metabolism vol.* pp. 415–425. Ed M. J Favus. Philadelphia: Lippincott Williams and Wilkins.

Wani M. R. Fuller K. Kim N. S. Choi Y & Chambers T (1999): Prostaglandin $E_2$ cooperates with TRANCE in osteoclast induction from hemopoietic precursors. Synergistic activation of differentiation, cell spreading and fusion. *Endocrinology* 140, 1927–1935.

Watts, N. B (1999). Pharmacology of agents to treat osteoporosis. *In Primer on the Metabolic Bone Diseases and Disorders of Mineral Metabolism* pp. 278–283 Ed M. J Favus. Philadelphia: Lippincott Williams and Wilkins.

We claim:

1. A method of inhibiting osteoclast formation comprising contacting bone marrow cells with a composition comprising at least about 10 µg/mL of mussel hydrolysate and at least one additive, wherein said mussel hydrolysate is formed by a process comprising:
- fermenting meat and mantle fluid of Indian green mussel with a proteolytic enzyme at a constant temperature thereby forming a thick paste;
- contacting the past with an acid;
- adjusting the resulting solution to room temperature and adding a base to maintain pH; and
- incubating the resulting solution in a separating flask thereby forming a middle layer containing said mussel hydrolysate.

2. The method of claim 1, wherein the additive(s) is selected from the group consisting of carbohydrates, sugar, proteins, fats, water, and a pharmaceutically acceptable carrier.

3. The method of claim 1, wherein at least one additive is a pharmaceutically acceptable excipient.

4. The method of claim 1, wherein at least one additive is a pharmaceutically acceptable diluent.

5. The method of claim 1, wherein the Indian green mussel is *Perna viridis*.

6. The method of claim 1, wherein inhibition of mononuclear TRAP-positive osteoclast formation is at least about 20%.

7. The method of claim 6, wherein inhibition of mononuclear TRAP-positive osteoclast formation is at least about 50%.

8. The method of claim 1, wherein inhibition of multinuclear TRAP-positive osteoclast formation is at least about 20%.

9. The method of claim 8, wherein inhibition of multinuclear TRAP-positive osteoclast formation is at least about 50%.

10. The method of claim 1, wherein inhibition of osteoclast formation is measured as inhibition of formation of osteoclasts from murine hemopoietic cells.

11. The method of claim 1, wherein the concentration of mussel hydrolysate is between about 10 µg/mL and about 100 µg/mL.

12. The method of claim 1, wherein the concentration of mussel hydrolysate is greater than about 100 µg/mL.

13. A method of inhibiting bone resorption comprising contacting bone marrow cells with a composition comprising at least about 10 µg/mL of mussel hydrolysate and at least one additive, wherein said mussel hydrolysate is formed by a process comprising:

fermenting meat and mantle fluid of Indian green mussel with a proteolytic enzyme at a constant temperature thereby forming a thick paste;

contacting the past with an acid;

adjusting the resulting solution to room temperature and adding a base to maintain pH; and incubating the resulting solution in a separating flask thereby forming a middle layer containing said mussel hydrolysate.

14. The method of claim 13, wherein the additive is selected from the group consisting of carbohydrates, sugar, proteins, fats, water, and pharmaceutically accepted carrier.

15. The method of claim 13, wherein the additive is a pharmaceutically acceptable excipient.

16. The method of claim 13, wherein the additive is a pharmaceutically acceptable diluent.

17. The method of claim 13, wherein the Indian green mussel is *Perna viridis*.

18. The method of claim 13, wherein the concentration of mussel hydrolysate is between about 10 µg/mL and about 100 µg/mL.

19. The method of claim 13, wherein the concentration of mussel hydrolysate is greater than about 100 µg/mL.

20. The method of claim 13, wherein inhibition is measured as inhibition of RANKL-induced bone resorption.

21. The method of claim 20, wherein inhibition of RANKL-induced bone resorption is at least about 40%.

22. The method of claim 21, wherein inhibition of RANKL-induced bone resorption is at least about 70%.

23. The method of claim 1, wherein the proteolytic enzyme is protosubtiline.

24. The method of claim 13, wherein the proteolytic enzyme is protosubtiline.

\* \* \* \* \*